US012643911B2

(12) United States Patent (10) Patent No.: US 12,643,911 B2

Chang et al. (45) Date of Patent: Jun. 2, 2026

(54) PROCESS FOR PREPARING RELUGOLIX AND INTERMEDIATES THEREOF

(71) Applicant: ScinoPharm Taiwan, Ltd., Tainan (TW)

(72) Inventors: Yung-Hung Chang, Tainan (TW); Tsung-Yu Hsiao, Tainan (TW); Meng-Fen Ho, Tainan (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 367 days.

(21) Appl. No.: 18/312,526

(22) Filed: May 4, 2023

(65) Prior Publication Data

US 2023/0357267 A1 Nov. 9, 2023

Related U.S. Application Data

(60) Provisional application No. 63/338,641, filed on May 5, 2022.

(51) Int. Cl.
    *C07D 495/04* (2006.01)
    *C07D 333/38* (2006.01)
    *C07D 409/12* (2006.01)

(52) U.S. Cl.
    CPC ......... *C07D 495/04* (2013.01); *C07D 333/38* (2013.01); *C07D 409/12* (2013.01)

(58) Field of Classification Search
    CPC ... C07D 495/04; C07D 333/38; C07D 409/12
    See application file for complete search history.

(56) References Cited

U.S. PATENT DOCUMENTS

| | | |
|---|---|---|
| 7,300,935 B2 | 11/2007 | Cho et al. |
| 9,758,528 B2 | 9/2017 | Fukuoka et al. |
| 2024/0317773 A1* | 9/2024 | Guo ..................... C07D 495/04 |

FOREIGN PATENT DOCUMENTS

| | | | |
|---|---|---|---|
| CN | 110194776 A | 9/2019 | |
| CN | 111333633 A | 4/2020 | |
| CN | 112321602 A | 2/2021 | |
| WO | 2000056739 | 9/2000 | |
| WO | 2014-051164 A2 | 4/2014 | |
| WO | WO 2022/170737 A1 * | 8/2022 | ........... C07D 495/04 |

OTHER PUBLICATIONS

International Search Report mailed on Aug. 7, 2023, for PCT Application No. PCT/SG2023/050298, filed May 2, 2023, 12 pages.
Pitushkin, D.A. et al., "Synthesis and properties of 1,3-distributed ureas and their isosteric analogs containing polycyclic fragments: V.1 1-(Bicyclo[2.2.1]heptan-2-yl)-3-R-and 1-(1,7,7-Tricyclo[2.2.1]heptan-2-yl)-3-R-ureas", Russian Journal of Organic Chemistry, 2020, vol. 56, No. 11. pp. 1893-1904.

Miwa, K. et al., "Discovery of 1-{4-[1-(2,6-Difluorobenzyl)-5-[(dimethylamino)methyl]-3-(6-methoxypyridazin-3-yl)-2,4-dioxo-1,2,3,4-tetrahydrothieno[2,3-d]pyrimidin-6-yl]phenyl}-3-methoxyurea (TAK-385) as a Potent, OrallyActive, Non-Peptide Antagonist of the Human Gonadotropin-ReleasingHormone Receptor", J. Med. Chem. 2011, vol. 54, No. 14, pp. 4998-5012.

* cited by examiner

*Primary Examiner* — Rebecca L Anderson

(74) *Attorney, Agent, or Firm* — Mintz Levin Cohn Ferris Glovsky and Popeo, P.C.

(57) ABSTRACT

The present disclosure provides improved processes for the preparation of Relugolix and intermediates thereof. Relugolix is prepared via intermediates (M7) and (M8):

wherein X is as described herein. Present disclosure also provides three additional routes to prepare Relugolix and intermediates thereof, where the starting material of ethyl 2-amino-4-methyl-5-(4-nitrophenyl)thiophene-3-carboxylate (SM1) is protected by coupling with an acyl chloride, a hydroxylamine or an oxime.

21 Claims, 8 Drawing Sheets

Relugolix

Relugolix

PROCESS FOR PREPARING RELUGOLIX AND INTERMEDIATES THEREOF

CROSS-REFERENCES TO RELATED APPLICATIONS

This application claims priority to U.S. Provisional Application No. 63/338,641 filed May 5, 2022, which is incorporated herein in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

Relugolix (brand name Orgovyx) is a gonadotropin-releasing hormone antagonist (GnRH receptor antagonist) medication, which is used in the treatment of prostate cancer in men and uterine fibroids in women.

Relugolix is resented by formula (I):

(I)

Relugolix has the chemical name of "1-(4-(1-(2,6-difluorobenzyl)-5-((dimethylamino)methyl)-3-(6-methoxypyridazin-3-yl)-2,4-dioxo-1,2,3,4-tetrahydrothieno[2,3-d]pyrimidin-6-yl)phenyl)-3-methoxyurea" or "N-[4-[1 [(2,6-Difluorophenyl)meth  yl]-5-[(dimethylamino)methyl]-1,2,3,4-tetrahydro-3-(6-methoxy-3-pyridazinyl)-2,4-dioxothieno[2,3-d]pyrimidin-6-yl]phenyl]-N'-methoxyurea".  Relugolix has a molecular formula of $C_{29}H_{27}F_2N_7O_5S$ and a molecular weight of 623.63 Da.

U.S. Pat. No. 7,300,935 discloses the preparation of Relugolix as shown in FIG. 1. Compound (5) of FIG. 1 is prepared in five (5) steps according to Reference Example 17 of WO 2000/056739 as follows: Step (1)—compound (1) is constructed from nitrophenylacetone via Gewald aminothiophene sysnthetis; Step (2)—compound (2) is obtained by carbamate formation using ethyl chloroformate; Step (3)—compound (3) is generated by alkylation with 2,6-difluorobenzylchloride; Step (4)—compound (4) is produced by selective bromination of compound (3) at 4-methyl group using NBS/AIBN; and Step (5)—compound (5) is formed by N-alkylation with (2-methoxyethyl)methylamine.

Accordingly, as shown in FIG. 1, Relugolix is prepared from compound (5) as follows: Step (6)—compound (5) is reduced via hydrogenation by Pd/C to provide compound (6); Step (7)—the generated $NH_2$ group in compound (6) undergoes condensation with methoxyamine using CDI as coupling reagent, leading to carbamide species of compound (7); Step (8)—hydrolysis of compound (7) with KOH results in the formation of compound (8); Steps (9) and (10)—the bicyclic scaffold of compound (10) is formed by coupling reaction of compound (8) with 3-amino-6-methoxy-pyridazine, followed by cyclization of compound (9) with NaOMe; and Step (11)—finally, compound 10 is converted to Relugolix by using 1-chloroethylchloroformate and dimethylamine. See U.S. Pat. No. 7,300,935, Reference Examples 5-7, Example 57, and Reference Example 55.

U.S. Pat. No. 9,758,528 discloses another synthetic pathway for the preparation of Relugolix and its intermediates as shown in FIG. 2. It involves directly introduction of dimethylamine instead of (2-methoxyethyl)methylamine to generate compound (5'), followed by hydrolysis to give compound (6'). Amide coupling of compound (6') with 3-amino-6-methoxypyridazine leads to the formation of compound (7'), followed by cyclization with NaOMe to afford compound (8'). Compound 8' is reduced via hydrogenation by Pd/C to give compound (9'). The generated $NH_2$ group in compound (9') undergoes condensation with methoxyamine using CDI as coupling reagent, leading to Relugolix.

Chinese Patent Application No. 111,333,633 discloses an alternative route for the preparation of Relugolix and its intermediates as shown in FIG. 3.

Chinese Patent Application No. 112,321,602 has demonstrated another route of preparing Relugolix, as shown in FIG. 4. The main difference between FIG. 3 (i.e., the process of CN 111,333,633) and FIG. 4 (i.e., the process of CN 112,321,602) is in the sequence of attaching the side chain of —NHC(O)NHOMe of the thiophene moiety.

Despite the above described processes, there remains a need for the development of improved processes for the preparation of Relugolix. The present disclosure addresses this need and provides related advantages as well.

BRIEF SUMMARY

In a first aspect, the present disclosure provides a process for preparing Relugolix, represented by formula (I):

(I)

or a salt thereof via intermediates (M7) and (M8). The process includes:

a) combining a compound of formula (M7):

(M7)

or a salt thereof, with a carbonylating agent in a solvent to form a compound of formula (M8):

(M8)

or a salt thereof; and
b) converting the compound or salt of formula (M8) to Relugolix of formula (I) or the salt thereof,
wherein the carbonylating agent is carbonyl diimidazole (CDI) or disuccinimidyl carbonate; and X is imidazoyl or O-succinimidyl, respectively, or the carbonylating agent is a chloroformate selected from the group consisting of $CH_3OC$ (O)Cl, $CH_3CH_2OC(O)Cl$, phenyl-OC(O)Cl, or 4-nitrophenyl-OC(O)Cl; and X is $OCH_3$, $OCH_2CH_3$, O-phenyl, or O-4-nitrophenyl, respectively.

In a second aspect, the present disclosure provides a process for preparing Relugolix, represented by formula (I) or a salt thereof from the intermediate (M8). The process includes:
b) combining a compound of formula (M8):

(M8)

or a salt thereof, with methoxyamine or a salt thereof to provide Relugolix of formula (I) or the salt thereof, wherein X is imidazoyl, O-succinimidyl, $OCH_3$, $OCH_2CH_3$, O-phenyl, or O-4-nitrophenyl.

In a third aspect, the present disclosure provides a process for preparing Relugolix, represented by formula (I) or a salt thereof via intermediates (M5) to (M8). The process includes:
vi) combining a compound of formula (M5)

(M5)

or a salt thereof, with 6-methoxypyridazin-3-amine to form a compound of formula (M6):

(M6)

or a salt thereof;
vii) hydrogenating the compound or salt of formula (M6) with a hydrogen source to provide a compound of formula (M7):

(M7)

or a salt thereof;
a) combining the compound or salt of formula (M7) with a carbonylating agent in a solvent to form a compound of formula (M8):

(M8)

or a salt thereof; and b) converting the compound or salt of formula (M8) to Relugolix of formula (I) or the salt thereof, wherein the carbonylating agent is carbonyl diimidazole (CDI) or disuccinimidyl carbonate; and X is imidazoyl or O-succinimidyl, respectively, or the carbonylating agent is a chloroformate selected from the group consisting of CH₃OC(O)Cl, CH₃CH₂OC(O)Cl, phenyl-OC(O)Cl, or 4-nitrophenyl-OC(O)Cl; and X is OCH₃, OCH₂CH₃, O-phenyl, or O-4-nitrophenyl, respectively.

In a fourth aspect, the present disclosure provides a compound, selected from the group consisting of:

(M1)

(M2)

(M3)

6

-continued (M4)

(M5)

(M6)

(M7)

(M8)

-continued (M8-1)

or a salt thereof, wherein, in formula (M8), X is imidazoyl, O-succinimidyl, $OCH_3$, $OCH_2CH_3$, O-phenyl, or O-4-nitro-phenyl.

In a fifth aspect, the present disclosure provides a compound, selected from the group consisting of:

(M1')

(M2')

(M3')

, and (M4')

, a salt thereof, wherein:

R is $C_{1-4}$ alkyl, O—$NR^1R^2$, or O—N=$CR^3R^4$;

$R^1$ and $R^2$ are independently hydrogen, tert-butyloxycarbonyl (Boc), $C_{1-4}$ alkyl, or phenyl; and $R^3$ and $R^4$ are independently hydrogen, $C_{1-4}$ alkyl, or phenyl.

BRIEF DESCRIPTION OF THE DRAWINGS

Figure 1:
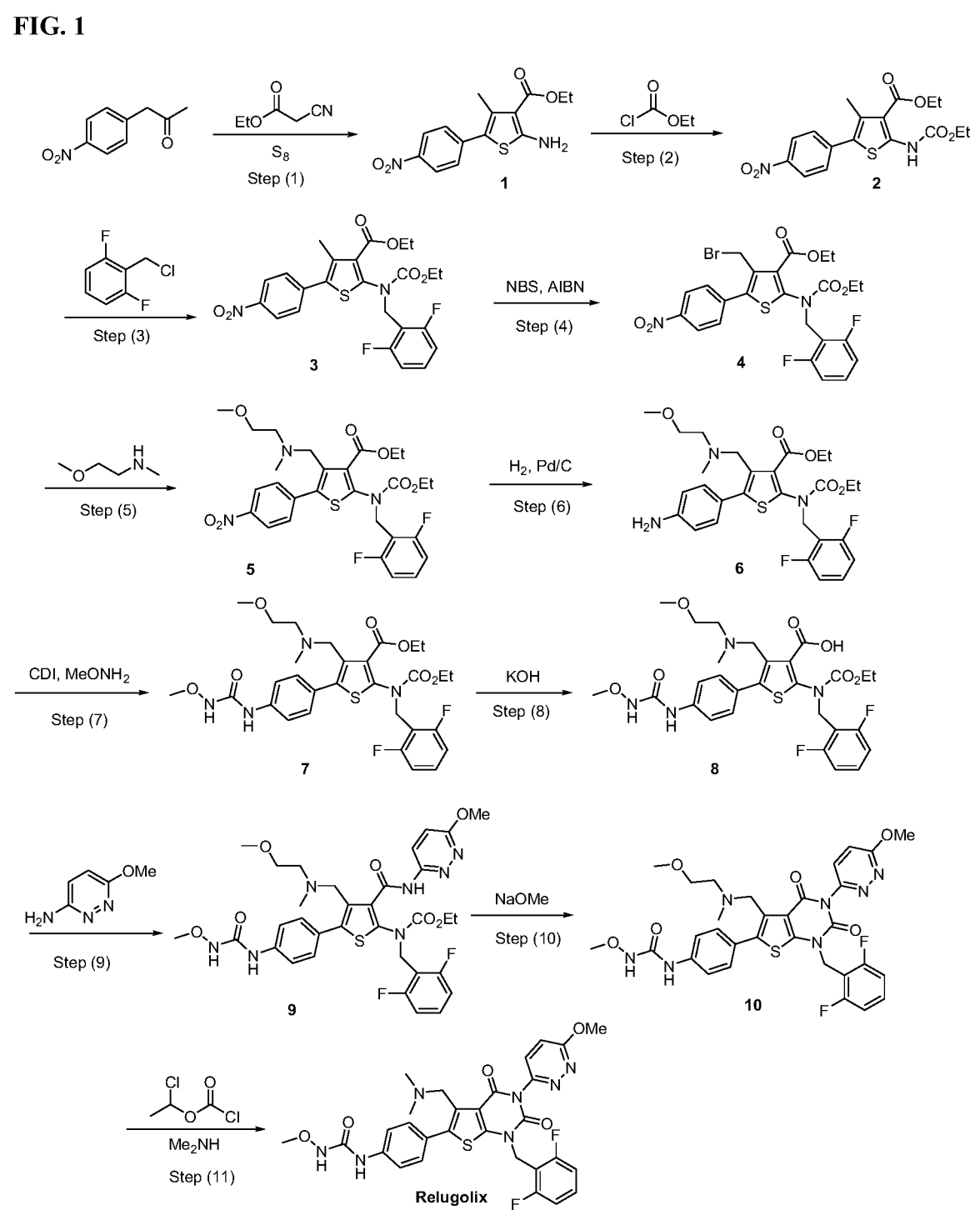

FIG. 1 shows the preparation of Relugolix as disclosed in U.S. Pat. No. 7,300,935.

Figure 2:
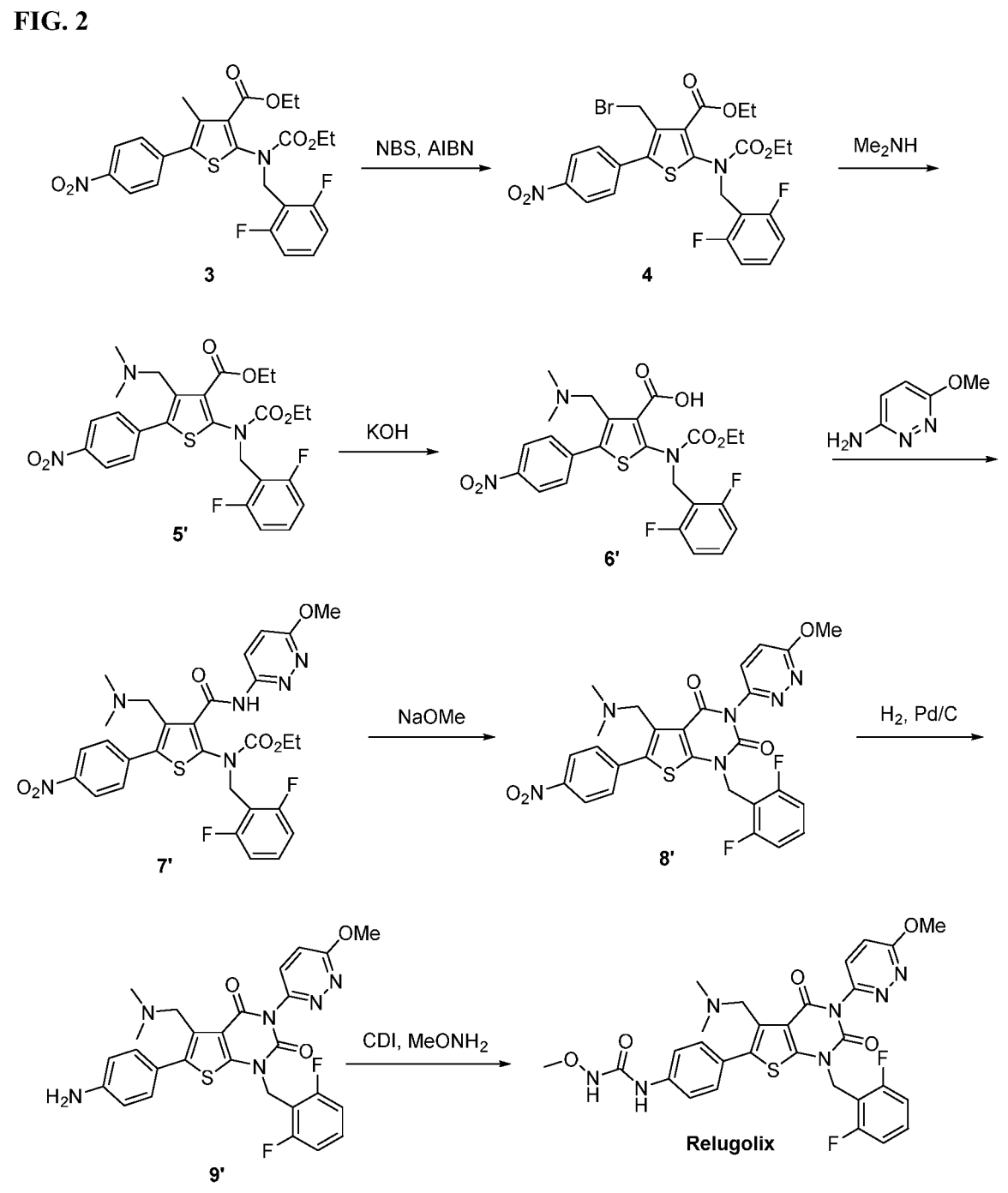

FIG. 2 shows the preparation of Relugolix as disclosed in U.S. Pat. No. 9,758,528.

Figure 3:
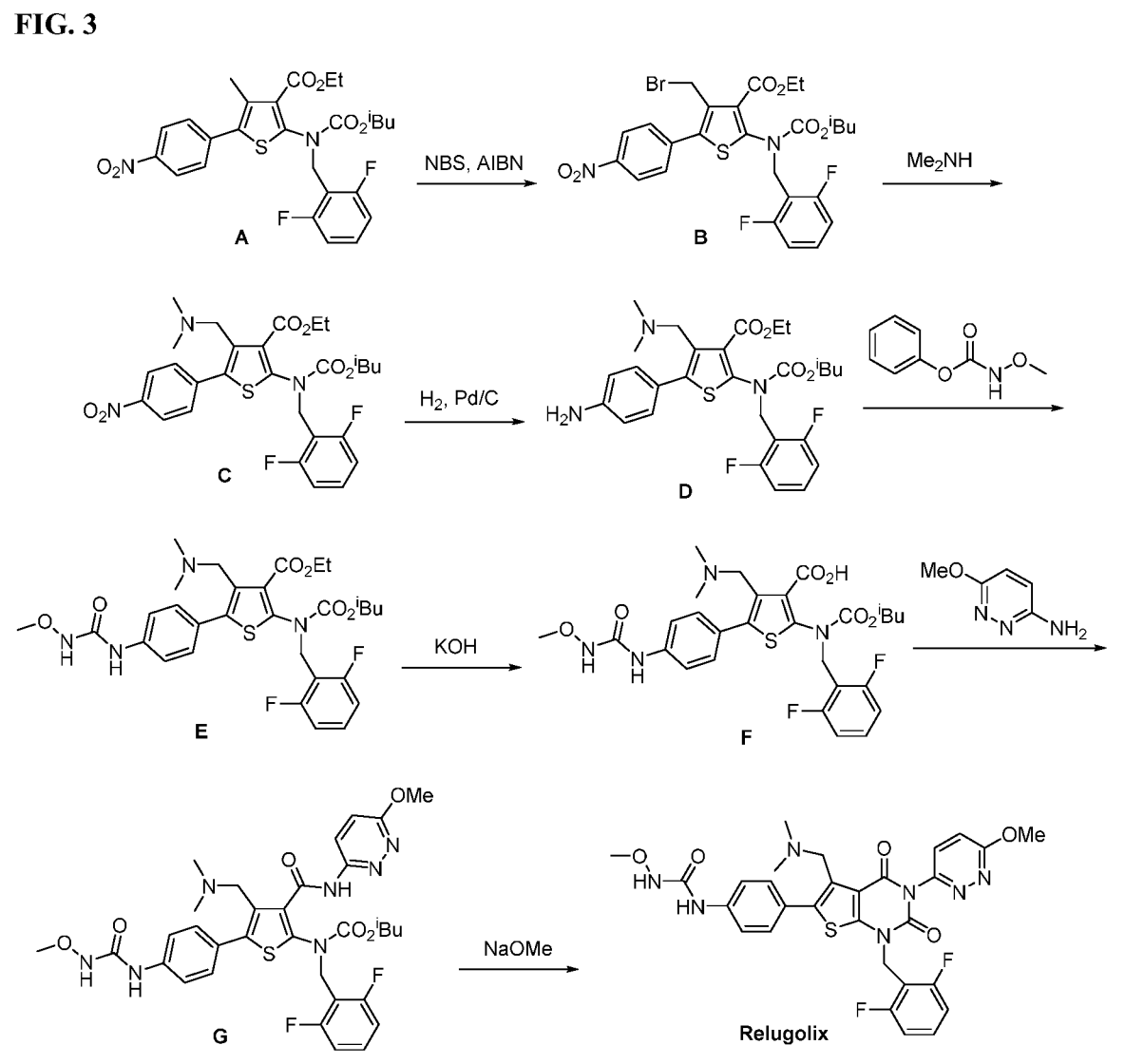

FIG. 3 shows the preparation of Relugolix as disclosed in Chinese Patent Application No. 111,333,633.

Figure 4:
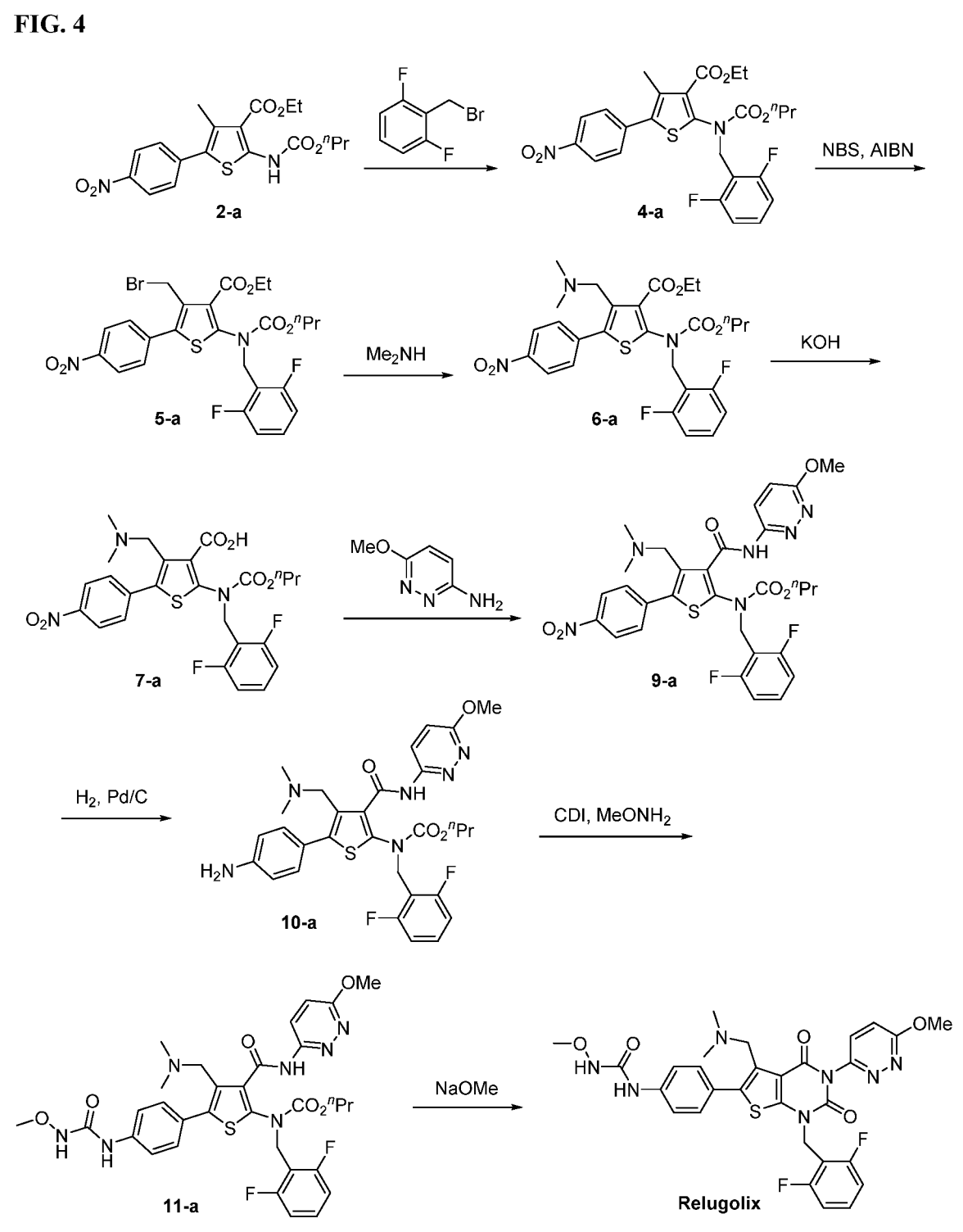

FIG. 4 shows the preparation of Relugolix as disclosed in Chinese Patent Application No. 112,321,602.

FIG. 5 shows the preparation of Relugolix via synthetic route-1.

FIG. 6 shows the preparation of Relugolix via synthetic route-2.

FIG. 7 shows the preparation of Relugolix via synthetic route-3.

FIG. 8 shows the preparation of Relugolix via synthetic route-4.

DETAILED DESCRIPTION

I. General

The present disclosure provides improved processes for the preparation of Relugolix and intermediates thereof. Relugolix is prepared according to synthetic routes 1-4 of FIGS. 5-8, via intermediates (M5) to (M8), in particular intermediates (M7) and (M8). Accordingly, intermediate (M7) is reacted with a carbonylating agent (e.g., CDI) to form intermediate (M8), for example intermediate (M8-1). Following the reaction of intermediate (M8) (e.g., intermediate (M8-1)) with methoxyamine hydrochloride or methoxyamine free base to provide Relugolix. Present disclosure also provides three additional routes (synthetic route-2, route-3, and route-4) to prepare Relugolix and intermediates thereof, where the starting material of ethyl 2-amino-4-methyl-5-(4-nitrophenyl)thiophene-3-carboxylate (SM1) is protected by coupling with an acyl chloride (e.g., acetyl chloride), a hydroxylamine (e.g., N-Boc-N-methylhydroxylamine), or an oxime (e.g., benzophenone oxime). Accordingly, as shown FIGS. 6-8, Relugolix is prepared via intermediates (M5) to (M8) starting from intermediates (i.e., M1'-1 to M'4-1, M1'-2 to M4'-2, or M1'-3 to M4'-3).

II. Definitions

Unless otherwise specified, the substitute, represented by in all formulae of the present disclosure (e.g., formulae in claims, embodiments, and FIGS. 1-8) refers to a methyl group.

"Salt" refers to acid or base salts of the compounds used in the methods of the present disclosure. Salts useful in the present disclosure include, but are not limited to, phosphate, sulfate, chloride, bromide, carbonate, nitrate, acetate, methanesulfonate, sodium, potassium, and calcium salts. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts, and alkali metal or alkali earth metal salts (sodium, potassium, calcium, and the like). It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Base" refers to a functional group that deprotonates water to produce a hydroxide ion. Bases useful in the present disclosure include organic bases and inorganic bases. Exemplary organic bases include tertiary amines and alkali alkoxides, as defined herein. Exemplary inorganic bases include alkali bicarbonates, alkali carbonates, and alkali hydroxides, as defined herein.

"Tertiary amine" refers to a compound having formula $N(R)_3$ wherein the R groups can be alkyl, aryl, heteroalkyl, heteroaryl, among others, or two R groups together form a N-linked heterocycloalkyl. The R groups can be the same or different. Non-limiting examples of tertiary amines include triethylamine, tri-n-butylamine, N,N-diisopropylethylamine, N-methylpyrrolidine, N-methylmorpholine, dimethylaniline, diethylaniline, 1,8-bis(dimethylamino)naphthalene, quinuclidine, and 1,4-diazabicylo[2.2.2]-octane (DABCO).

"Amidine-based compounds" herein refers to a class of chemical compounds that include, but are not limited to, 1,8-diazabicyclo[5.4.0]undec-7-ene (DBU) and 1,5-diazabicyclo[4.3.0]non-5-ene (DBN).

"Alkali bicarbonate" refers to a class of chemical compounds which are composed of an alkali metal cation and the hydrogencarbonate anion ($HCO_3^-$). Alkali carbonates useful in the present disclosure include lithium bicarbonate ($LiHCO_3$), sodium bicarbonate ($NaHCO_3$), potassium bicarbonate ($KHCO_3$), and cesium bicarbonate ($CsHCO_3$).

"Alkali carbonate" refers to a class of chemical compounds which are composed of an alkali metal cation and the carbonate anion ($CO_3^{2-}$). Alkali carbonates useful in the present disclosure include lithium carbonate ($Li_2CO_3$), sodium carbonate ($Na_2CO_3$), potassium carbonate ($K_2CO_3$), and cesium carbonate ($Cs_2CO_3$).

"Strong base" includes an alkali alkoxide as defined herein.

"Alkali hydroxide" refers to a class of chemical compounds which are composed of an alkali metal cation and the hydroxide anion ($OH^-$). Alkali hydroxides useful in the present disclosure include lithium hydroxide (LiOH), sodium hydroxide (NaOH), potassium hydroxide (KOH), cesium hydroxide (CsOH), and calcium hydroxide ($Ca(OH)_2$).

"Alkali alkoxide" refers to a class of chemical compounds which are composed of an alkali metal cation and the alkoxide anion ($RO^-$), wherein R is $C_{1-4}$ alkyl. Alkali alkoxides useful in the present disclosure include, but are not limited to, sodium isopropoxide, sodium methoxide, sodium tert-butoxide, potassium tert-butoxide, and potassium isopropoxide.

"Combining" refers to the process of bringing at least two distinct species together such that they can react. It should be appreciated, however, the resulting reaction product can be produced directly from a reaction between the added reagents or from an intermediate from one or more of the added reagents which can be produced in the reaction mixture.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, toluene, diethyl ether, and 1,4-dioxane. Other solvents are useful in the present disclosure.

"Carbonylating agent" refers to a reagent capable of adding a carbonyl group, —C(O)—, to a compound. Representing carbonylating agents include, but are not limited to, phosgene or a phosgene equivalent (e.g., diphosgene, triphosgene, carbonyl diimidazole (CDI), and disuccinimidyl carbonate), or a chloroformate (e.g., $CH_3OC(O)Cl$, $CH_3CH_2OC(O)Cl$, phenyl-OC(O)Cl, 4-nitrophenyl-OC(O)Cl, or succinimidyl chloroformate).

"Trifluroacetylating agent" refers to a reagent capable of adding a trifluoroacetyl group, —$C(O)CF_3$, to a compound. Representing trifluroacetylating agents include, but are not limited to, trifluoroacetic anhydride (TFAA) and trifluoroacetyl chloride.

"Brominating agent" refers to a reagent capable of adding a bromo group, —Br, to a compound. Representative brominating agents include, but are not limited to, bromine, N-bromosuccinimide, triphenylphosphine dibromide, tetrabutylammonium tribromide, trimethylphenylammonium tribromide, N-bromoacetamide, pyridinium tribromide, dibromodimethylhydantoin, tribromoisocyanuric acid, N-bromosaccharin, and 1,2-dibromo-1,1,2,2-tetrachloroethane.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

III. Processes

In a first aspect, the present disclosure provides a process for preparing Relugolix, represented by formula (I):

(I)

or a salt thereof via intermediates (M7) and (M8). The process includes:

a) combining a compound of formula (M7):

(M7)

or a salt thereof, with a carbonylating agent in a solvent to form a compound of formula (M8):

(M8)

or a salt thereof; and b) converting the compound or salt of formula (M8) to Relugolix of formula (I) or the salt thereof, wherein the carbonylating agent is carbonyl diimidazole (CDI) or disuccinimidyl carbonate; and X is imidazoyl or O-succinimidyl, respectively, or the carbonylating agent is a chloroformate selected from the group consisting of $CH_3OC$ (O)Cl, $CH_3CH_2OC(O)Cl$, phenyl-OC(O)Cl, or 4-nitrophe-nyl-OC(O)Cl; and X is $OCH_3$, $OCH_2CH_3$, O-phenyl, or O-4-nitrophenyl, respectively.

In a second aspect, the present disclosure provides a process for preparing Relugolix, represented by formula (I) or a salt thereof from the intermediate (M8). The process includes:

b) combining a compound of formula (M8):

(M8)

or a salt thereof, with methoxyamine or a salt thereof to provide Relugolix of formula (I) or the salt thereof, wherein X is imidazoyl, O-succinimidyl, $OCH_3$, $OCH_2CH_3$, O-phenyl, or O-4-nitrophenyl.

In some embodiments, step a) further includes a base, which is a tertiary amine and/or an amidine-based compound. In some embodiments, the tertiary amine is triethylamine, tri-n-butylamine, N,N-diisopropylethylamine, N-methylpyrrolidine, N-methylmorpholine, dimethylani-line, diethylaniline, 1,8-bis(dimethylamino)naphthalene, quinuclidine, 1,4-diazabicylo[2.2.2]-octane (DABCO), or a mixture thereof. In some embodiments, the amidine-based compound is 1,8-diazabicyclo[5.4.0]undec-7-ene (DBU), 1,5-diazabicyclo[4.3.0]non-5-en (DBN), a mixture thereof. In some embodiments, step a) further includes 1,8-diazabi-cyclo[5.4.0]undec-7-ene (DBU).

With reference to step a), in some embodiments, the carbonylating agent is carbonyl diimidazole (CDI) or dis-uccinimidyl carbonate. In some embodiments, the carbo-nylating agent is carbonyl diimidazole (CDI). In some embodiments, the carbonylating agent is disuccinimidyl carbonate. In some embodiments, the carbonylating agent is a chloroformate selected from the group consisting of $CH_3OC(O)Cl$, $CH_3CH_2OC(O)Cl$, phenyl-OC(O)Cl, or 4-ni-trophenyl-OC(O)Cl.

In some embodiments, the carbonylating agent is carbo-nyl diimidazole (CDI) or disuccinimidyl carbonate; and X in formula (M8) is imidazoyl or O-succinimidyl, respectively. In some embodiments, the carbonylating agent is carbonyl diimidazole (CDI); and X in formula (M8) is imidazoyl. In some embodiments, the carbonylating agent is disuccinim-idyl carbonate; and X in formula (M8) is O-succinimidyl. In some embodiments, the carbonylating agent is a chlorofor-mate selected from the group consisting of $CH_3OC(O)Cl$, $CH_3CH_2OC(O)Cl$, phenyl-OC(O)Cl, or 4-nitrophenyl-OC (O)Cl; and X in formula (M8) is $OCH_3$, $OCH_2CH_3$, O-phe-nyl, or O-4-nitrophenyl, respectively.

In some embodiments, X in formula (M8) is imidazoyl; and the compound of formula (M8) is a compound repre-sented by formula (M8-1):

(M8-1)

or a salt thereof.

In some embodiments, the carbonylating agent is carbo-nyl diimidazole (CDI); X in formula (M8) is imidazoyl; and the compound of formula (M8) is the compound or salt of formula (M8-1).

With reference to step a), in some embodiments, the solvent is an aprotic solvent. Suitable aprotic solvents include tetrahydrofuran (THF), 2-methyl-tetrahydrofuran (2-MeTHF), ethyl acetate (EtOAc), dimethylformamide (DMF), dichloromethane (DCM), toluene, dimethylacet-amide(DMAc), isopropyl acetate (IPAc), acetonitrile, or mixtures thereof. In some embodiments, the solvent is an aprotic solvent selected from the group consisting of tetra-hydrofuran (THF), 2-methyl-tetrahydrofuran (2-MeTHF), ethyl acetate (EtOAc), dimethylformamide (DMF), dichloromethane (DCM), toluene, dimethylacetamide(DMAc), isopropyl acetate (IPAc), acetonitrile, or mixtures thereof. In some embodiments, the solvent is THF.

With reference to step b), in some embodiments, step b) is conducted without isolating the compound of formula (M8) or the salt thereof. In some embodiments, the compound of formula (M8) or the salt thereof is prepared in situ. In some embodiments, step b) is conducted without isolating the compound of formula (M8-1) or the salt thereof. In some embodiments, the compound of formula (M8-1) or the salt thereof is prepared in situ.

In general, step b) can be performed by combining the compound of formula (M8) or the salt thereof (e.g., formed in step a)) and methoxyamine or a salt thereof in any order. In some embodiments, Relugolix of formula (I) or the salt thereof is formed by: 1) addition of the compound of formula (M8) or the salt thereof (e.g., formed in step a)) to methoxyamine or a salt thereof; or 2) addition of methoxyamine or a salt thereof into the compound of formula (M8) or the salt thereof (e.g., formed in step a)).

In some embodiments, a mixture of step a) including the compound of formula (M8) or the salt thereof is added to methoxyamine or a salt thereof to form Relugolix of formula (I) or the salt thereof. In some embodiments, a mixture of step a) including the compound of formula (M8) or the salt thereof is added to a solution of methoxyamine or a salt thereof to form Relugolix of formula (I) or the salt thereof. In some embodiments, the solution of methoxyamine or a salt thereof is formed in the same solvent of step a). In some embodiments, a mixture of step a) includes the compound of formula (M8-1) or the salt thereof and THF; and the solution of methoxyamine or a salt thereof includes methoxyamine and THF.

In some embodiments, methoxyamine or a salt thereof is added to a mixture of step a) including the compound of formula (M8) or the salt thereof to form Relugolix of formula (I) or the salt thereof. In some embodiments, methoxyamine hydrochloride is added to a mixture of step a) including the compound of formula (M8-1) or the salt thereof to form Relugolix of formula (I) or the salt thereof.

In general, step a) can be performed at any suitable temperature. In some embodiments, steps a) is conducted at a temperature of from 20° C. to 50° C. In some embodiments, step a) is conducted at room temperature.

In general, step b) can be performed at any suitable temperature. In some embodiments, steps b) is conducted at a temperature of from 20° C. to 50° C. In some embodiments, step b) is conducted at room temperature. In some embodiments, step b) is conducted in THF at room temperature.

In some embodiments, Relugolix is isolated in a yield of at least about 85% or about 90% in two steps (i.e., steps a) and b). In some embodiments, Relugolix is isolated via steps a) and b) with a yield of at least about 90% (e.g., 92.9%). In some embodiments, Relugolix is isolated via steps a) and b) with a yield of about 92.9%.

In some embodiments, prior to step a), the process further includes steps vi) to vii):

vi) combining a compound of formula (M5)

(M5)

or a salt thereof, with 6-methoxypyridazin-3-amine to form a compound of formula (M6):

(M6)

or a salt thereof;

vii) hydrogenating the compound or salt of formula (M6) with a hydrogen source to provide a compound of formula (M7):

(M7)

or a salt thereof.

In a third aspect, the present disclosure provides a process for preparing Relugolix, represented by formula (I) or a salt thereof via intermediates (M5) to (M8). The process includes:

vi) combining a compound of formula (M5)

(M5)

or a salt thereof, with 6-methoxypyridazin-3-amine to form a compound of formula (M6):

(M6)

or a salt thereof;

vii) hydrogenating the compound or salt of formula (M6) with a hydrogen source to provide a compound of formula (M7):

(M7)

or a salt thereof;

a) combining the compound or salt of formula (M7) with a carbonylating agent in a solvent to form a compound of formula (M8):

(M8)

or a salt thereof; and b) converting the compound or salt of formula (M8) to Relugolix of formula (I) or the salt thereof, wherein the carbonylating agent is carbonyl diimidazole (CDI) or disuccinimidyl carbonate; and X is imidazoyl or O-succinimidyl, respectively, or the carbonylating agent is a chloroformate selected from the group consisting of $CH_3OC(O)Cl$, $CH_3CH_2OC(O)Cl$, phenyl-OC(O)Cl, or 4-nitrophenyl-OC(O)Cl; and X is $OCH_3$, $OCH_2CH_3$, O-phenyl, or O-4-nitrophenyl, respectively.

With reference to step vi), in some embodiments, step vi) is conducted with 6-methoxypyridazin-3-amine and an amide coupling reagent in an aprotic solvent. In some embodiments, step vi) is conducted with 6-methoxy-pyridazin-3-amine and 1-ethyl-3-(3-dimethylaminopropyl) carbodiimide (EDCI) in DCM. In some embodiments, step vi) is conducted in DCM at room temperature. In some embodiments, the compound of formula (M6) is isolated with a yield of >90% (e.g., 91%).

With reference to step vii), in some embodiments, the hydrogen source is hydrogen gas. In some embodiments, step vii) is conducted with hydrogen gas over 10% Pd/C in an alcohol (e.g., MeOH). In some embodiments, step vii) is conducted with hydrogen gas over 10% Pd/C in methanol (MeOH). In some embodiments, step vii) is conducted with hydrogen gas over 10% Pd/C in the presence of an acid (e.g., 32% HCl) in methanol (MeOH). In some embodiments, step vii) is conducted with hydrogen gas over 10% Pd/C in the presence of HCl (e.g., 32% HCl) in methanol (MeOH). In some embodiments, step vii) is conducted at room temperature. In some embodiments, the compound of formula (M7) is isolated with a yield of >95% (e.g., 96%).

Steps a) and b) are as described herein.

IIIA. Synthetic Route-1

Relugolix of formula (I) or a salt thereof can be prepared in nine (9) steps as follows:

Steps i) to v) via intermediates (M1) to (M4) to provide intermediate (M5);

Steps vi) and vii) via intermediates (M5) and (M6) to provide intermediate (M7); and Finally, steps a) and b) via intermediates (M7) and (M8) to provide Relugolix of formula (I) or a salt thereof.

Figure 5:
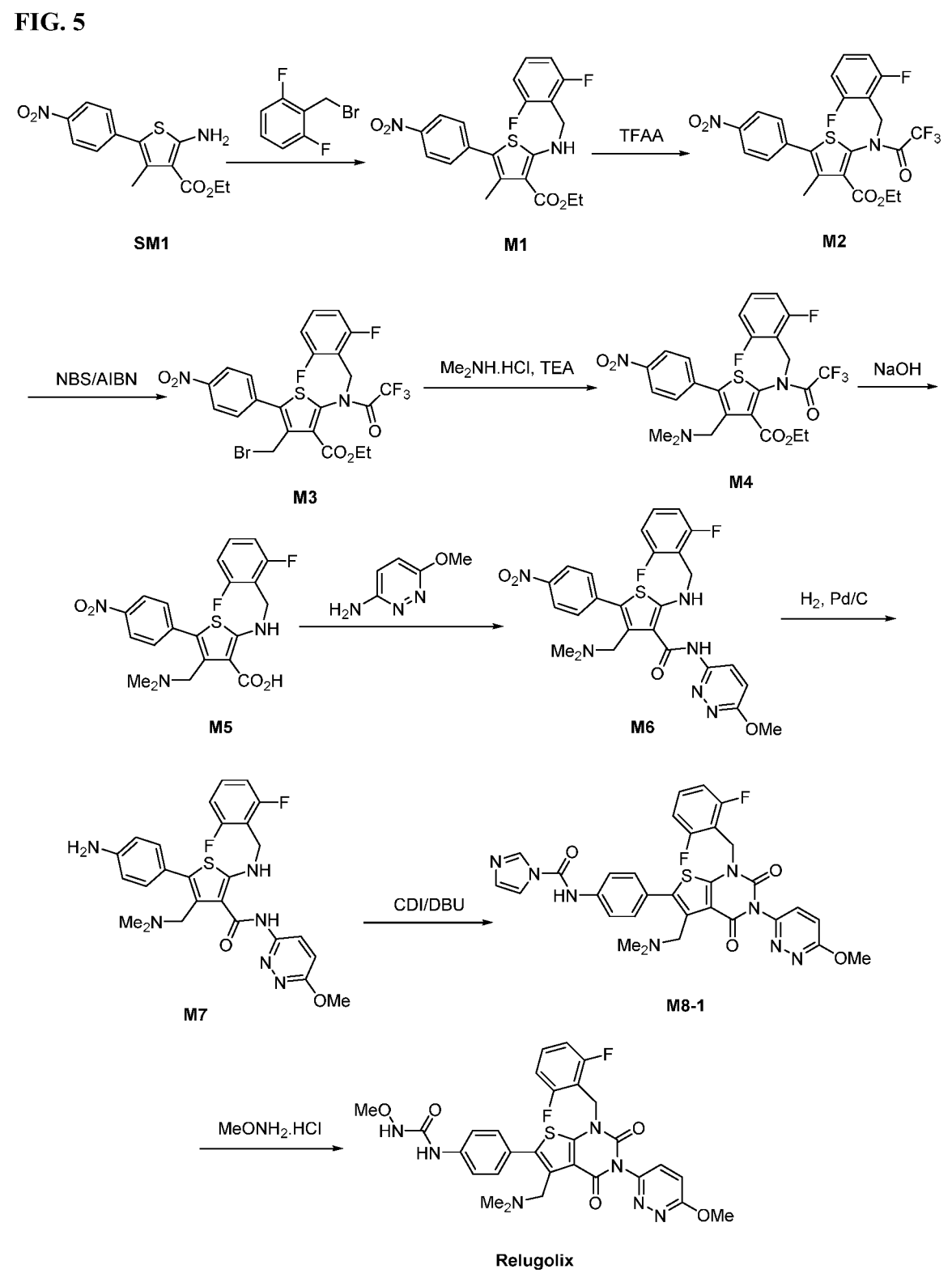

FIG. 5 shows a representative synthetic scheme for this route.

In some embodiments, prior to step a), the process further includes steps i) to vii):

i) combining a compound of formula (SM1):

(SM1)

or a salt thereof, with 2,6-difluorobenzyl bromide or 2,6-difluorobenzyl chloride to form a compound of formula (M1):

(M1)

or a salt thereof;

ii) combining the compound or salt of formula (M1) with a trifluoroacetylating agent to form a compound of formula (M2):

(M2)

or a salt thereof;

iii) brominating the compound or salt of formula (M2) with a brominating agent to form a compound of formula (M3):

(M3)

or a salt thereof;

iv) combining the compound or salt of formula (M3) with dimethylamine or a salt thereof to provide a compound of formula (M4):

(M4)

or a salt thereof;

v) hydrolyzing the compound or salt of formula (M4) with a base to provide a compound of formula (M5):

(M5)

or a salt thereof;

vi) combining the compound or salt of formula (M5) with 6-methoxypyridazin-3-amine to form a compound of formula (M6):

(M6)

or a salt thereof; and vii) hydrogenating the compound or salt of formula (M6) with a hydrogen source to provide the compound or salt of formula (M7):

(M7)

With reference to step i), in some embodiments, step i) is conducted with 2,6-difluorobenzyl bromide in an aprotic solvent. In some embodiments, step i) is conducted with 2,6-difluorobenzyl bromide in dimethylacetamide (DMAc). In some embodiments, step i) is conducted at a temperature of about 80° C. In some embodiments, the compound of formula (M1) is isolated with a yield of >90% (e.g., about 94%).

With reference to step ii), in some embodiments, step ii) is conducted with the trifluoroacetylating agent and a tertiary amine in an aprotic solvent. In some embodiments, the trifluroacetylating agent is trifluoroacetic anhydride (TFAA). In some embodiments, step ii) is conducted with trifluoroacetic anhydride (TFAA) and triethylamine (TEA) in dichloromethane (DCM). In some embodiments, step ii) is conducted at a temperature of about 25° C. In some embodiments, the compound of formula (M2) is isolated with a yield of >90% (e.g., about 95%).

With reference to step iii), in some embodiments, step iii) is conducted with the brominating agent and a radical initiator (e.g., azobisisobutyronitrile) in an aprotic solvent. In some embodiments, the brominating agent is N-bromosuccinimide. In some embodiments, step iii) is conducted with N-bromosuccinimide and azobisisobutyronitrile (AIBN) in a mixture of ethyl acetate (EtOAc) and trifluorotoluene. In some embodiments, step iii) is conducted at a temperature of about 70° C. In some embodiments, the compound of formula (M3) is isolated with a yield of about 90%.

With reference to step iv), in some embodiments, step iv) is conducted with dimethylamine or dimethylamine hydrochloride and a tertiary amine in an aprotic solvent. In some embodiments, step iv) is conducted with dimethylamine hydrochloride and trimethylamine in dimethylacetamide (DMAc). In some embodiments, step iv) is conducted at a temperature of from about 0° C. to room temperature. In some embodiments, the compound of formula (M4) is converted to a hydrochloride (HCl) salt thereof. In some embodiments, the compound of formula (M4) in a HCl salt is isolated with a yield of >95% (e.g., 98%).

With reference to step v), in some embodiments, step v) is conducted with alkali hydroxide in an alcohol. In some embodiments, the alkali hydroxide is sodium hydroxide. In some embodiments, sodium hydroxide is in an aqueous solution. In some embodiments, the step v) is conducted with an aqueous solution of sodium hydroxide in ethanol (EtOH). In some embodiments, step v) is conducted at a temperature of from about 70° C. to about 80° C. In some embodiments, the compound of formula (M5) is isolated with a yield of >90% (e.g., 92%).

With reference to step vi), in some embodiments, step vi) is conducted with 6-methoxypyridazin-3-amine and an amide coupling reagent in an aprotic solvent. In some embodiments, step vi) is conducted with 6-methoxypyridazin-3-amine and 1-ethyl-3-(3-dimethylaminopropyl) carbodiimide (EDCI) in DCM. In some embodiments, step vi) is conducted in DCM at room temperature. In some embodiments, the compound of formula (M6) is isolated with a yield of >90% (e.g., 91%).

With reference to step vii), in some embodiments, the hydrogen source is hydrogen gas. In some embodiments, step vii) is conducted with hydrogen gas over 10% Pd/C in an alcohol (e.g., MeOH). In some embodiments, step vii) is conducted with hydrogen gas over 10% Pd/C in methanol (MeOH). In some embodiments, step vii) is conducted with hydrogen gas over 10% Pd/C in the presence of an acid (e.g., 32% HCl) in methanol (MeOH). In some embodiments, step vii) is conducted with hydrogen gas over 10% Pd/C in the presence of HCl (e.g., 32% HCl) in methanol (MeOH). In some embodiments, step vii) is conducted at room temperature. In some embodiments, the compound of formula (M7) is isolated with a yield of >95% (e.g., 96%).

In one aspect, the present disclosure provides a process for preparing a compound of formula (M1) according to step i), a compound of formula (M2) according to step ii) or steps i)-ii), a compound of formula (M3) according to step iii) or steps i)-iii), a compound of formula (M4) according to step iv) or steps i)-iv), a compound of formula (M5) according to step v) or steps i)-v), a compound of formula (M6) according to step vi) or steps i)-vi), or a compound of formula (M7) according to step vii) or steps i)-vii), each of which is defined and described herein.

In another aspect, the present disclosure provides a process for preparing Relugolix of formula (I) or a salt thereof according to steps i) to vii) and steps a) and b), each of which is defined and described herein.

IIIB. Synthetic Route-2, Route-3, and Route 4

Relugolix of formula (I) or a salt thereof can be prepared in nine (9) steps as follows:

Steps i-1) to v-1) via intermediates (M1') to (M4') to provide intermediate (M5);

Steps vi) and vii) via intermediates (M5) and (M6) to provide intermediate (M7); and Finally, steps a) and b) via intermediates (M7) and (M8) to provide Relugolix of formula (I) or a salt thereof.

Figure 6:
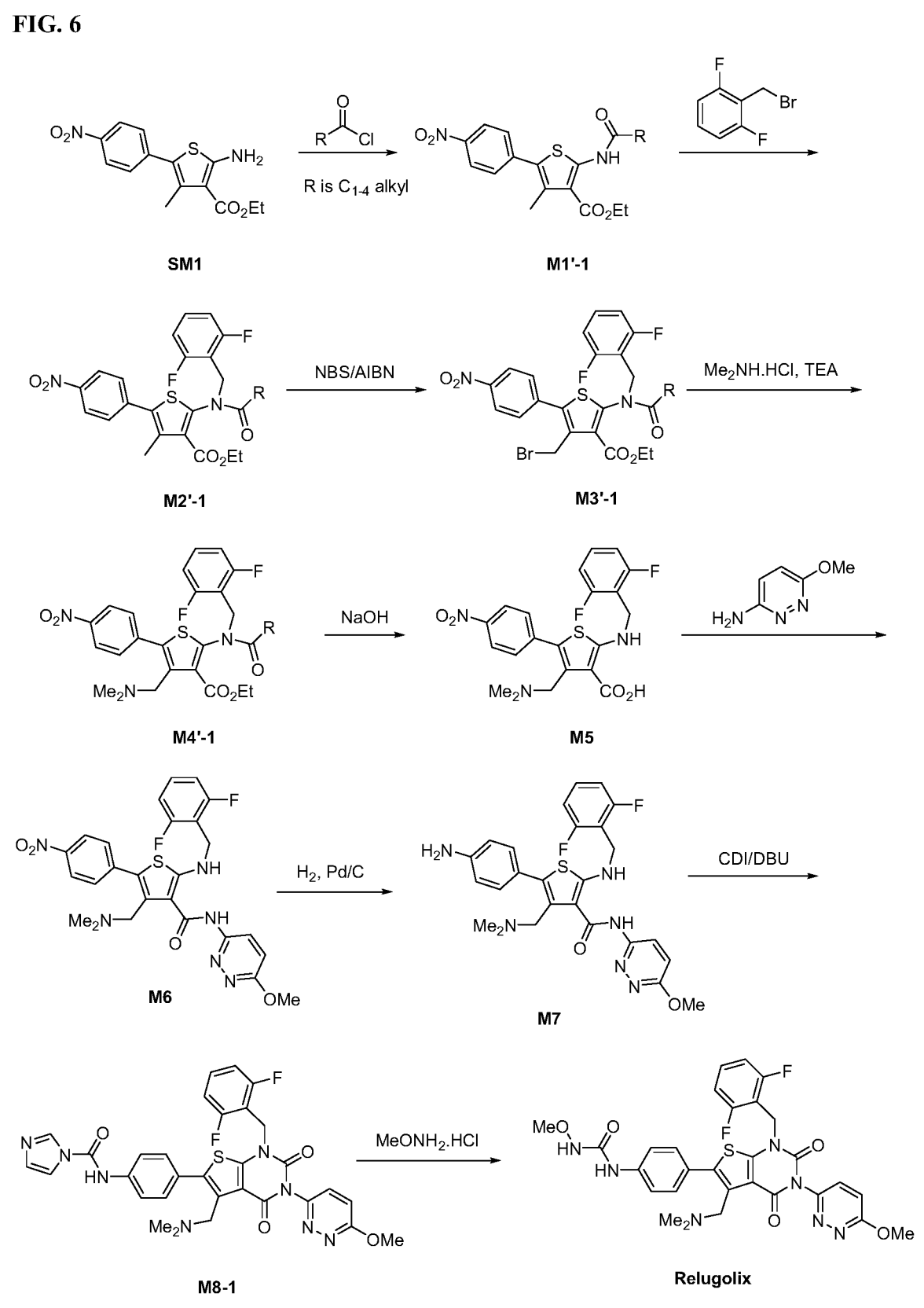
Figure 7:
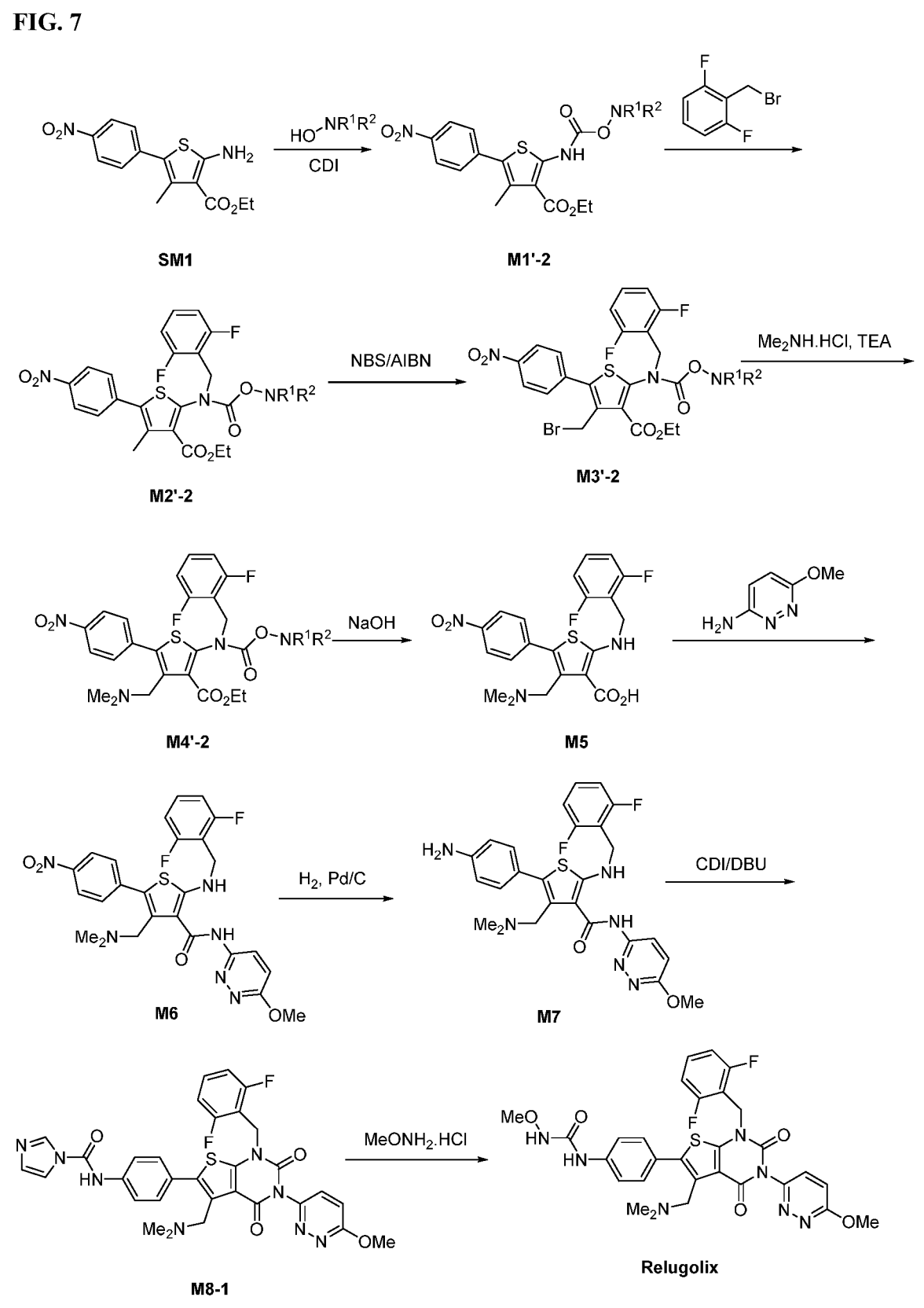
Figure 8:
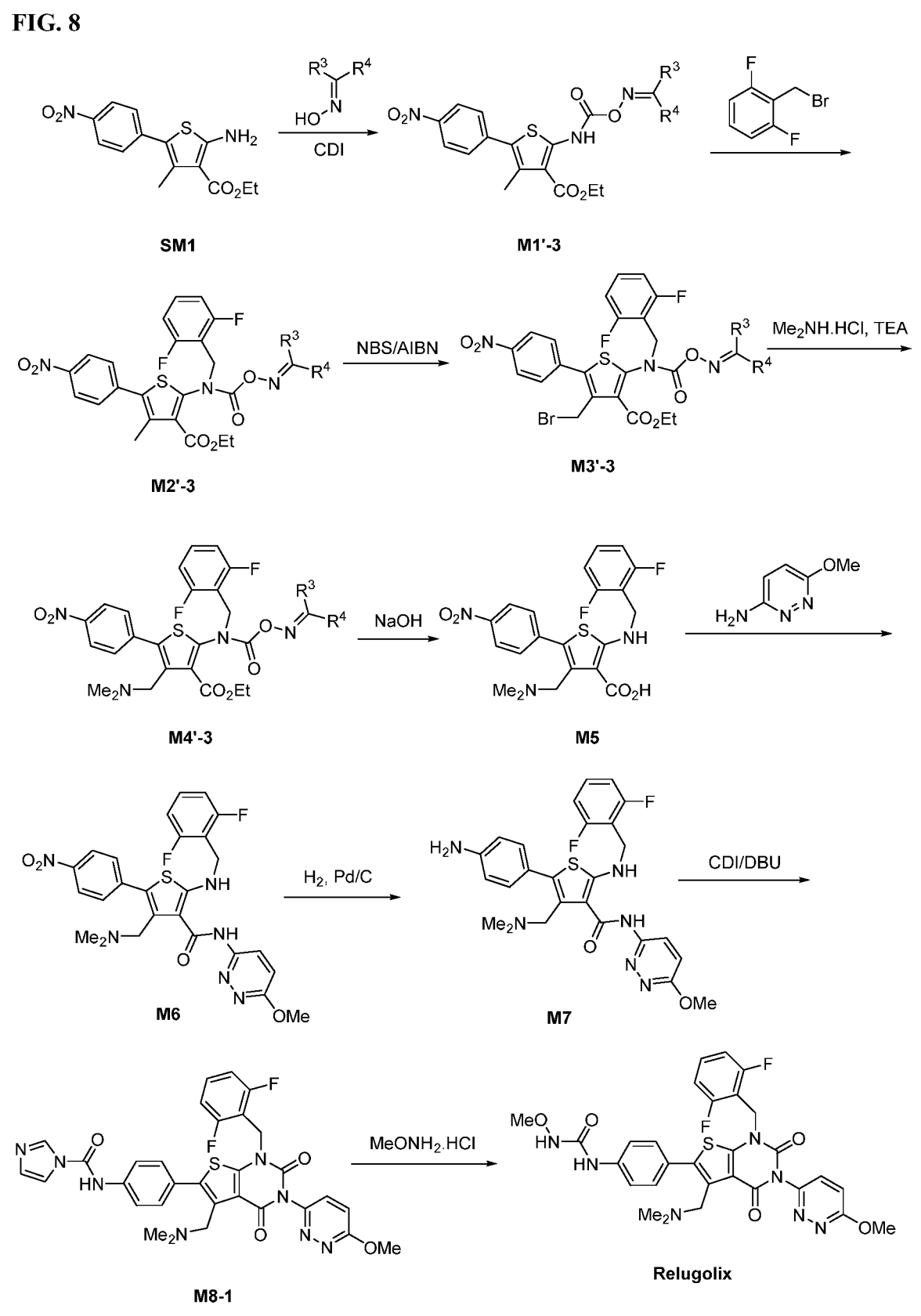

FIGS. 6-8 show representative synthetic schemes for those routes.

In some embodiments, prior to step vi), the process further includes steps i-1) to vii-1):

i-1) combining a compound of formula (SM1):

(SM1)

or a salt thereof, with a compound SM2 of $C_{1-4}$ alkyl-C(O)Cl or a combination of a carbonylating agent and a compound SM2 of a hydroxylamine or an oxime to form a compound of formula (M1'):

(M1')

O_2N— (structure) —NH—C(O)—R,
Me    CO_2Et or a salt thereof;

ii-1) combining the compound or salt of formula (M1')
with 2,6-difluorobenzyl bromide or 2,6-difluorobenzyl
chloride to form a compound of formula (M2'):

(M2')

O_2N— (structure) —N(CH_2-2,6-difluorophenyl)—C(O)—R
Me    CO_2Et or a salt thereof;

iii-1) brominating the compound or salt of formula (M2')
with a brominating agent to form a compound of
formula (M3'):

(M3')

O_2N— (structure) —N(CH_2-2,6-difluorophenyl)—C(O)—R
Br—CH_2    CO_2Et or a salt thereof;

iv-1) combining the compound or salt of formula (M3')
with dimethylamine or a salt thereof to provide a
compound of formula (M4'):

(M4')

O_2N— (structure) —N(CH_2-2,6-difluorophenyl)—C(O)—R
Me_2N—CH_2    CO_2Et or a salt thereof;

v-1) hydrolyzing the compound or salt of formula (M4')
with a base to provide the compound or salt of formula
(M5):

(M5)

O_2N— (structure) —NH—CH_2-(2,6-difluorophenyl)
Me_2N—CH_2    CO_2H wherein:

the hydroxylamine is represented by HO—NR$^1$R$^2$; and
the oxime is represented by HO—N$=$CR$^3$R$^4$;

in any one of formulae M1' to M4', R is C$_{1-4}$ alkyl,
O—NR$^1$R$^2$, or O—N$=$CR$^3$R$^4$;

R$^1$ and R$^2$ are independently hydrogen, tert-butyloxycar-
bonyl (Boc), C$_{1-4}$ alkyl, or phenyl; and R$^3$ and R$^4$ are independently hydrogen, C$_{1-4}$ alkyl, or
phenyl.

With reference to step i-1), in some embodiments, the
compound SM2 is C$_{1-4}$ alkyl-C(O)Cl. In some embodi-
ments, the compound SM2 is acetyl chloride.

With reference to step i-1), in some embodiments, the
compound SM2 is the hydroxylamine or oxime; and the
carbonylating agent is carbonyl diimidazole (CDI), disuc-
cinimidyl carbonate, CH$_3$OC(O)Cl, CH$_3$CH$_2$OC(O)Cl, phe-
nyl-OC(O)Cl, or 4-nitrophenyl-OC(O)Cl. In some embodi-
ments, the carbonylating agent is carbonyl diimidazole
(CDI) or disuccinimidyl carbonate. In some embodiments,
the carbonylating agent is carbonyl diimidazole (CDI). In
some embodiments, the hydroxylamine is N-Boc-N-meth-
ylhydroxylamine. In some embodiments, the oxime is ben-
zophenone oxime.

With reference to step ii-1), in some embodiment, step
ii-1) is conducted with 2,6-difluorobenzyl bromide in dim-
ethylacetamide (DMAc).

With reference step iii-1), in some embodiments, the
brominating agent is N-bromosuccinimide. In some embodi-
ments, step iii-1) is conducted with N-bromosuccinimide
and azobisisobutyronitrile in a solvent including ethyl
acetate (EtOAc).

With reference to step iv-1), in some embodiments, step
iv-1) is conducted with dimethylamine or dimethylamine
hydrochloride and triethylamine in dimethylacetamide
(DMAc).

With reference to step v-1), in some embodiments, the
step v-1) is conducted with sodium hydroxide in ethanol
(EtOH).

With reference to step i-1), in some embodiments, the
compound SM is C$_{1-4}$ alkyl-C(O)Cl; and the compound of
any one of formulae (M1') to (M4') is represented by a
compound of any one of formulae (M1'-1) to (M4'-1),
respectively:

(M1'-1)

O_2N— (structure) —NH—C(O)—C$_{1-4}$ alkyl,
CH_3    CO_2Et

-continued (M1'-1)

(M3'-1)

(M4'-1)

or a salt thereof.

With reference to step i-1), in some embodiments, the compound SM is acetyl chloride and the compound of any one of formulae (M1'-1) to (M4'-1) is represented by a compound of any one of formulae (M1'-1a) to (M4'-1a), respectively:

(M1'-1a)

(M2'-1a)

-continued (M3'-1a)

(M4'-1a)

or a salt thereof.

With reference to step i-1), in some embodiments, the compound SM2 is the hydroxylamine or oxime; and the compound of any one of formulae (M1') to (M4') is represented by a compound of any one of formulae (M1'-2) to (M4'-2) and (M1'-3) to (M4'-3), respectively:

(M1'-2)

(M2'-2)

(M3'-2)

-continued (M4'-2)

(M1'-3)

(M2'-3)

(M3'-3)

(M4'-3)

or a salt thereof, wherein $R^1$ and $R^2$ are independently hydrogen, tert-butyloxycarbonyl (Boc), $C_{1-4}$ alkyl, or phenyl; and $R^3$ and $R^4$ are independently hydrogen, $C_{1-4}$ alkyl, or phenyl.

With reference to step i-1), in some embodiments, the hydroxylamine is N-Boc-N-methylhydroxylamine; and the compound of any one of formulae (M1'-2) to (M4'-2) is represented by a compound of any one of formulae (M1'-2a) to (M4'-2a), respectively:

(M1'-2a)

(M2'-2a)

(M3'-2a)

, and (M4'-2a)

, or a salt thereof.

With reference to step i-1), in some embodiments, the oxime is benzophenone oxime; and the compound of any one of formulae (M1'-3) to (M4'-3) is represented by a compound of any one of formulae (M1'-3a) to (M4'-3a), respectively:

(M1'-3a)

27

-continued (M2'-3a)

(M3'-3a)

(M4'-3a)

or a salt thereof.

IV. Compounds

In a fourth aspect, the present disclosure provides a compound, selected from the group consisting of:

(M1)

(M2)

28

-continued (M3)

(M4)

(M5)

(M6)

(M7)

-continued (M8)

(M8-1)

or a salt thereof, wherein, in formula (M8), X is imidazoyl, O-succinimidyl, $OCH_3$, $OCH_2CH_3$, O-phenyl, or O-4-nitro-phenyl.

In a fifth aspect, the present disclosure provides a compound, selected from the group consisting of:

(M1')

(M2')

(M3')

-continued (M4')

a salt thereof, wherein:

R is $C_{1-4}$ alkyl, $O-NR^1R^2$, or $O-N=CR^3R^4$;

$R^1$ and $R^2$ are independently hydrogen, tert-butyloxycar-bonyl (Boc), $C_{1-4}$ alkyl, or phenyl; and $R^3$ and $R^4$ are independently hydrogen, $C_{1-4}$ alkyl, or phenyl.

In some embodiments, the compound is selected from the group consisting of:

(M1'-1a)

(M2'-1a)

(M3'-1a)

(M4'-1a)

-continued (M1'-2a)

(M2'-2a)

(M3'-2a)

, and (M4'-2a)

(M1'-3a)

(M2'-3a)

-continued (M3'-3a)

(M4'-3a)

or a salt thereof.

V. Examples

Example 1: Preparation of Relugolix Via Synthetic Route-1

The synthetic route-1 for the preparation of Relugolix is described in FIG. 5.

In synthetic route-1, alkylation of SM1 with 2,6-difluo-robenzylchloride affords M1, followed by amidation with TFAA to give M2. In the presence of AIBN as radical initiator, reaction of M2 with NBS could undergo selectively bromination at methyl group to generate M3. And then, the bromo group in M3 could be substituted by dimethylamine hydrochloride using triethylamine as base to afford M4. M4 could be hydrolyzed with NaOH to generated M5, followed by coupling reaction with 3-amino-6-methoxypyridazine to give M6. The nitro group in M6 could be hydrogenated with Pd/C to form M7. The activation of $NH_2$ group in M7, followed by cyclization could be activated by CDI/DBU to generate M8-1. Finally, relugolix could be synthesized via the reaction of M8-1 with methoxyamine hydrochloride.

Preparation of M1

SM1

-continued

M1

Preparation of M3

M2

To a suitable reactor, SM1 (10.0 g), 2,6-difluorobenzyl bromide (8.12 g) and DMAc (100 mL) were added. The resulting mixture was heated to 80° C. and then stirred overnight. Upon completion, the reaction was cooled to room temperature, followed by addition of NaHCO₃ aqueous solution (200 mL). The resulting slurry was stirred at room temperature for 1 hour. After filtration, the wet cake was washed with H₂O, and then dried at 60° C. under vacuum to afford M1 (13.3 g, 94% yield).

Preparation of M2

M1

M3

To a suitable reactor, M2 (10.0 g), EtOAc (40 mL) and trifluorotoluene (40 mL) were added. N-bromosuccinimide (4.21 g) and AIBN (0.31 g) were added thereto. The reaction mixture was heated to 70° C. and then stirred for 4 hours. Upon completion, the reaction was cooled to room temperature, and washed with H₂O (40 mL) twice. The organic layer was concentrated to 4 vol via solvent-swap with EtOH. n-Heptane (40 mL) was added slowly. The resulting suspension was cooled to 0° C. and then stirred for 1 hour. After filtration, the wet cake was washed with EtOH/n-heptane (20 mL, v/v=1/2) and then dried at 45° C. under vacuum to afford M3 (10.3 g, 90% yield).

Preparation of M4

M2

M3

M4•HCl

To a suitable reactor, M1 (5.0 g), DCM (50 mL) and triethylamine (4.5 mL) were added. The mixture was cooled to 0-10° C. TFAA (6.80 g) was added slowly. The resulting mixture was warmed to room temperature and then stirred for 12 hours. Upon completion, NaHCO₃ aqueous solution (100 mL) was added to quench. The solution was stirred at room temperature for 1 hour. After phase separation, the organic layer was washed with H₂O (50 mL) three times, followed by solvent swap with n-heptane to 3 vol. The resulting slurry was filtered through Buchner funnel. The wet cake was washed with n-heptane (15 mL) and then dried at 50° C. under vacuum to give M2 (5.83 g, 95% yield).

To a suitable reactor, M3 (12.0 g), dimethylamine hydrochloride (2.45 g) and DMAc (72 mL) was added. The mixture was cooled to 0-10° C. Triethylamine (5.28 g) was added dropwise. The resulting mixture was warmed to room temperature, and then stirred for 12 hours. Upon completion, IPAc (96 mL) and H$_2$O (48 mL) were added. After phase separation, the organic layer was washed with H$_2$O (48 mL), NaHCO3 aqueous solution (48 mL), and then H$_2$O (48 mL) sequentially. The organic layer was concentrated to 3 vol. via solvent swap with toluene. 32% HCl (2.26 g) in IPA (12 mL) was added. The resulting mixture was concentrated to 3 vol. via solvent swap with toluene. n-Heptane (36 mL) was added. The slurry was cooled to 0-10° C. and then stirred for 1 hour. After filtration, the wet cake was washed with toluene/n-heptane (30 mL, v/v=1/1), and then dried at 45° C. under vacuum to afford M4 hydrochloride (11.85 g, 98% yield).

Preparation of M5

M4·HCl

M5

To a suitable reactor, M4 hydrochloride (2.0 g) and EtOH (20 mL) was added. The mixture was heated to 55-60° C., followed by addition of 10% NaOH (5.9 mL). The mixture was heated to 70-80° C. and then stirred overnight. Upon completion, the solution was cooled to room temperature, followed by addition of H$_2$O (36 mL). The solution was neutralized with 1N HCl to pH 5-6. The resulting suspension was cooled to 0-10° C. and then stirred for 1 hour. After filtration, the wet cake was washed with H$_2$O (10 mL) and then dried at 60° C. under vacuum to afford M5 (1.36 g, 92% yield).

Preparation of M6

M5

-continued

M6

To a suitable reactor, M5 (5.00 g), 3-amino-6-methoxy-pyridazine (1.70 g), EDCI hydrochloride (4.29 g) and DCM (50 mL) were added. The mixture was stirred at room temperature overnight. Upon completion, H$_2$O (100 mL) was added. The mixture was stirred at room temperature for 1 hour. After phase separation, the organic layer was washed with H$_2$O (15 mL) twice and then concentrated to 3 vol. via solvent swap with IPA. H$_2$O (30 mL) was added to the resulting suspension. The mixture was stirred at room temperature for 1 hour. After filtration, the wet cake was washed with IPA/H$_2$O (15 mL, v/v=1/2) and then dried at 50° C. under vacuum to afford M6 (5.64 g, 910% yield).

Preparation of M7

M6

M7

To a suitable reactor, M6 (1.29 g) and MeOH (15 mL) were added. 32% HCl (0.64 mL) was charged, followed by addition of Pd/C (10 wt %). The mixture was stirred at room temperature under hydrogen pressure of 0.1-0.2 MPa overnight. Upon completion, the mixture was filtered through Buchner funnel containing Celite pad. The Celite pad was washed with MeOH (4 mL). The combined filtrates were concentrated to 5 vol., followed by addition of NaHCO₃ aqueous solution (8 mL). H₂O (6 mL) was added to the resulting suspension. The mixture was stirred at room temperature for 1 hour. After filtration, the wet cake was wash with MeOH/H₂O (4 mL, v/v=1/3) and then dried at 55° C. under vacuum to give M7 (1.17 g, 96% yield).

Preparation of Relugolix room temperature for 30 min. The resulting suspension was filtered through Bichner funnel to retain the solids. The organic layer was washed with H₂O (135 mL) three times. The organic layer was combined with above solids and then concentrated to 5 vol. via solvent swap with MeOH. The suspension was heated to reflux and then stirred for 1 hour. The suspension was cooled to room temperature and then stirred for 2 hours. After filtration, the wet cake was washed with MeOH/H₂O (81 mL, v/v=2/1) and then dried at 45° C. in vacuo to afford relugolix (29.8 g, 92.9% yield).

M7

M8-1

Relugolix

To a suitable reactor, M7 (27.0 g), CDI (27.5 g) and THF (216 mL) were charged, followed by addition of DBU (9.47 g). The mixture was stirred at room temperature for 3 hours. Upon completion, methoxyamine hydrochloride (21.6 g) and THF (162 mL) were added to another reactor, followed by addition of TEA (20.9 g). The above M8-1 solution was added slowly to the reactor containing methoxyamine. THF (54 mL) was added to rinse. The mixture was stirred at room temperature for 2 hrs. Upon completion, the reaction solution was concentrated to 5 vol. via solvent swap with EtOAc. EtOAc (270 mL) was added, followed by addition of 5% NaHCO₃ (405 mL). The resulting mixture was stirred at Example 2: Preparation of Relugolix Via Synthetic Route-2

The synthetic route-2 for the preparation of Relugolix is described in FIG. 6.

In synthetic route-2, SM1 was acetylated with acetyl chloride to generate M1'-1, followed by N-alkylation with 2,6-difluorobenzylbromide to give M2'-1. In the presence of AIBN as radical initiator, reaction of M2'-1 with NBS could undergo selectively bromination at methyl group to generate M3'-1. And then, the bromo group in M3'-1 could be substituted by dimethylamine to afford M4'-1. M5 could be obtained by the hydrolysis of M4'-1 as well. As described in synthetic route-1, relugolix could be obtained from M5.

Example 3: Preparation of Relugolix Via Synthetic Route-3 or Route 4

In synthetic route-3 or route-4, SM1 was coupled with hydroxylamine, such as N-Boc-N-methylhydroxylamine, or oxime, such as benzophenone oxime, using CDI to generate M1'-2 or M1'-3, followed by N-alkylation with 2,6-difluorobenzylchloride to give M2'-2 or M2'-3. In the presence of AIBN as radical initiator, reaction of M2'-2 or M2'-3 with NBS could undergo selectively bromination at methyl group to generate M3'-2 or M3'-3. And then, the bromo group in M3'-2 or M3'-3 could be substituted by dimethylamine to afford M4'-2 or M4'-3. M5 could be obtained by the hydrolysis of M4'-2 or M4'-3 as well. As described in synthetic route-1, relugolix can be obtained from M5.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing Relugolix, represented by formula (I):

(I)

or a salt thereof, comprising:
a) combining a compound of formula (M7):

(M7)

or a salt thereof, with a carbonylating agent in a solvent to form a compound of formula (M8):

(M8)

or a salt thereof; and
b) converting the compound or salt of formula (M8) to Relugolix of formula (I) or the salt thereof,
wherein the carbonylating agent is carbonyl diimidazole (CDI) or disuccinimidyl carbonate; and
X is imidazoyl or O-succinimidyl, respectively, or
the carbonylating agent is a chloroformate selected from the group consisting of
$CH_3OC(O)Cl$, $CH_3CH_2OC(O)Cl$, phenyl-OC(O)Cl, or 4-nitrophenyl-OC(O)Cl; and
X is $OCH_3$, $OCH_2CH_3$, O-phenyl, or O-4-nitrophenyl, respectively.

2. A process for preparing Relugolix, represented by formula (I):

(I)

or a salt thereof, comprising:
b) combining a compound of formula (M8):

(M8)

or a salt thereof, with methoxyamine or a salt thereof to provide Relugolix of formula (I) or the salt thereof, wherein X is imidazoyl, O-succinimidyl, $OCH_3$, $OCH_2CH_3$, O-phenyl, or O-4-nitrophenyl.

3. The process of claim 1, wherein the carbonylating agent is carbonyl diimidazole (CDI) and X is imidazoyl; or the carbonylating agent is disuccinimidyl carbonate and X is O-succinimidyl.

4. The process of claim 3, wherein the carbonylating agent is carbonyl diimidazole (CDI) and X is imidazoyl.

5. The process of claim 1, wherein X is imidazoyl; and the compound of formula (M8) is a compound represented by formula (M8-1):

(M8-1)

or a salt thereof.

6. The process of claim 1, wherein the solvent is an aprotic solvent selected from the group consisting of tetrahydrofuran (THF), 2-methyl-tetrahydrofuran (2-MeTHF), ethyl acetate (EtOAc), dimethylformamide (DMF), dichloromethane (DCM), toluene, dimethylacetamide(DMAc), isopropyl acetate (IPAc), acetonitrile, or mixtures thereof.

7. The process of claim 6, wherein the solvent is THF.

8. The process of claim 1, wherein step a) further comprises a base selected from the group consisting of triethylamine, tri-n-butylamine, N,N-diisopropylethylamine, N-methylpyrrolidine, N-methylmorpholine, dimethylaniline, diethylaniline, 1,8-bis(dimethylamino)naphthalene, quinuclidine, 1,4-diazabicyclo[2.2.2]-octane (DABCO), 1,8-diazabicyclo[5.4.0]undec-7-ene (DBU), 1,5-diazabicyclo [4.3.0]non-5-en (DBN), and a mixture thereof.

9. The process of claim 8, wherein step a) further comprises 1,8-diazabicyclo[5.4.0]undec-7-ene (DBU).

10. The process of claim 1, prior to step a), further comprising steps i) to vii):

i) combining a compound of formula (SM1):

(SM1)

or a salt thereof, with 2,6-difluorobenzyl bromide or 2,6-difluorobenzyl chloride to form a compound of formula (M1):

(M1)

or a salt thereof;

ii) combining the compound or salt of formula (M1) with a trifluoroacetylating agent to form a compound of formula (M2):

(M2)

or a salt thereof;

iii) brominating the compound or salt of formula (M2) with a brominating agent to form a compound of formula (M3):

(M3)

or a salt thereof;

iv) combining the compound or salt of formula (M3) with dimethylamine or a salt thereof to provide a compound of formula (M4):

(M4)

or a salt thereof;

v) hydrolyzing the compound or salt of formula (M4) with a base to provide a compound of formula (M5):

(M5)

or a salt thereof;

vi) combining the compound or salt of formula (M5) with 6-methoxypyridazin-3-amine to form a compound of formula (M6):

(M6)

or a salt thereof; and vii) hydrogenating the compound or salt of formula (M6) with a hydrogen source to provide the compound or salt of formula (M7):

(M7)

11. The process of claim 10, wherein:

in step ii), the trifluoroacetylating agent is trifluoroacetic anhydride (TFAA);

in step iii), the brominating agent is N-bromosuccinimide;

in step v), the base is sodium hydroxide; and in step vii), the hydrogen source is hydrogen gas.

12. The process of claim 10, wherein:

step i) is conducted with 2,6-difluorobenzyl bromide or 2,6-difluorobenzyl chloride in dimethylacetamide (DMAc);

step ii) is conducted with trifluoroacetic anhydride (TFAA) and triethylamine (TEA) in dichloromethane (DCM);

step iii) is conducted with N-bromosuccinimide and azo-bisisobutyronitrile in a mixture of ethyl acetate (EtOAc) and trifluorotoluene;

step iv) is conducted with dimethylamine hydrochloride and trimethylamine in dimethylacetamide (DMAc); optionally, converting to a HCl salt of the compound of formula (M4) by adding hydrochloride in isopropyl alcohol;

step v) is conducted with sodium hydroxide in ethanol (EtOH);

step vi) is conducted with 6-methoxypyridazin-3-amine and 1-ethyl-3-(3-dimethylaminopropyl)carbodiimide (EDCI) hydrochloride in dichloromethane (DCM); and step vii) is conducted with hydrogen gas over 10% Pd/C in methanol (MeOH).

13. A process for preparing Relugolix, represented by formula (I):

(I)

or a salt thereof, comprising:

vi) combining a compound of formula (M5)

(M5)

or a salt thereof, with 6-methoxypyridazin-3-amine to form a compound of formula (M6):

(M6)

or a salt thereof;

vii) hydrogenating the compound or salt of formula (M6) with a hydrogen source to provide a compound of formula (M7):

(M7)

or a salt thereof;

a) combining the compound or salt of formula (M7) with a carbonylating agent in a solvent to form a compound of formula (M8):

(M8)

or a salt thereof; and b) converting the compound or salt of formula (M8) to Relugolix of formula (I) or the salt thereof, wherein the carbonylating agent in step a) is carbonyl diimidazole (CDI) or disuccinimidyl carbonate; and X is imidazoyl or O-succinimidyl, respectively, or the carbonylating agent in step a) is a chloroformate selected from the group consisting of $CH_3OC(O)Cl$, $CH_3CH_2OC(O)Cl$, phenyl-OC(O)Cl, or 4-nitrophenyl-OC(O)Cl; and X is $OCH_3$, $OCH_2CH_3$, O-phenyl, or O-4-nitrophenyl, respectively.

14. The process of claim 13, prior to step vi), further comprising steps i-1) to vii-1):

i-1) combining a compound of formula (SM1):

(SM1)

or a salt thereof, with a compound of formula SM2 which is $C_{1-4}$ alkyl-C(O)Cl or a combination of a carbonylating agent and a compound of formula SM2 which is a hydroxylamine or an oxime to form a compound of formula (M1'):

(M1')

or a salt thereof;

ii-1) combining the compound or salt of formula (M1') with 2,6-difluorobenzyl bromide or 2,6-difluorobenzyl chloride to form a compound of formula (M2'):

(M2')

or a salt thereof;

iii-1) brominating the compound or salt of formula (M2') with a brominating agent to form a compound of formula (M3'):

(M3')

or a salt thereof;

iv-1) combining the compound or salt of formula (M3') with dimethylamine or a salt thereof to provide a compound of formula (M4'):

(M4')

or a salt thereof;

v-1) hydrolyzing the compound or salt of formula (M4') with a base to provide the compound or salt of formula (M5):

(M5)

wherein:

the hydroxylamine is represented by $HO—NR^1R^2$;

the oxime is represented by $HO—N=CR^3R^4$;

in any one of formulae M1' to M4', R is $C_{1-4}$ alkyl, $O—NR^1R^2$, or $O—N=CR^3R^4$;

$R^1$ and $R^2$ are independently hydrogen, tert-butyloxycarbonyl (Boc), $C_{1-4}$ alkyl, or phenyl; and $R^3$ and $R^4$ are independently hydrogen, $C_{1-4}$ alkyl, or phenyl.

15. The process of claim 14, wherein, in step i-1), the compound SM2 is the hydroxylamine or oxime; and the carbonylating agent is carbonyl diimidazole (CDI), disuccinimidyl carbonate, $CH_3OC(O)Cl$, $CH_3CH_2OC(O)Cl$, phenyl-OC(O)Cl, or 4-nitrophenyl-OC(O)Cl.

16. The process of claim 14, wherein:

in step i-1), the compound SM2 is acetyl chloride, the hydroxylamine is N-Boc-N-methylhydroxylamine, or the oxime is benzophenone oxime; or in step iii-1), the brominating agent is N-bromosuccinimide; and in step v-1), the base is sodium hydroxide.

17. The process of claim 14, wherein, in step i-1), the compound SM2 is $C_{1-4}$ alkyl-C(O)Cl; and the compound of any one of formulae (M1') to (M4') is represented by a compound of any one of formulae (M1'-1) to (M4'-1), respectively:

(M1'-1)

(M2'-1)

(M3'-1)

(M4'-1)

or a salt thereof.

18. The process of claim 17, wherein the compound SM is acetyl chloride and the compound of any one of formulae (M1'-1) to (M4'-1) is represented by a compound of any one of formulae (M1'-1a) to (M4'-1a), respectively:

(M1'-1a)

-continued (M2'-1a)

(M3'-1a)

, and (M4'-1a)

or a salt thereof.

19. The process of claim 14, wherein, in step i-1), the compound SM2 is the hydroxylamine or oxime; and the compound of any one of formulae (M1') to (M4') is represented by a compound of any one of formulae (M1'-2) to (M4'-2) and (M1'-3) to (M4'-3), respectively:

(M1'-2)

(M2'-2)

-continued (M3'-2)

(M4'-2)

(M1'-3)

(M2'-3)

(M3'-3)

51
-continued (M4'-3)

or a salt thereof, wherein R¹ and R² are independently hydrogen, tert-butyloxycarbonyl (Boc), $C_{1-4}$ alkyl, or phenyl; and R³ and R⁴ are independently hydrogen, $C_{1-4}$ alkyl, or phenyl.

20. The process of claim 19, wherein, in step i-1), the hydroxylamine is N-Boc-N-methylhydroxylamine; and the compound of any one of formulae (M1'-2) to (M4'-2) is represented by a compound of any one of formulae (M1'-2a) to (M4'-2a), respectively:

(M1'-2a)

(M2'-2a)

(M3'-2a)

52
-continued (M4'-2a)

or a salt thereof.

21. The process of claim 19, wherein, in step i-1), the oxime is benzophenone oxime; and the compound of any one of formulae (M1'-3) to (M4'-3) is represented by a compound of any one of formulae (M1'-3a) to (M4'-3a), respectively:

(M1'-3a)

(M2'-3a)

(M3'-3a)

-continued (M4'-3a)

or a salt thereof.

*   *   *   *   *

15